United States Patent [19]
Domes

[11] Patent Number: 5,420,743
[45] Date of Patent: May 30, 1995

[54] CONTROL OF THE NEUTRALIZATION OF SURFACE CHARGES ON OBJECTS

[75] Inventor: Helmut Domes, Stuttgart, Germany

[73] Assignee: Eastman Kodak Company, Rochester, N.Y.

[21] Appl. No.: 89,145

[22] Filed: Jul. 8, 1993

[30] Foreign Application Priority Data

Jul. 25, 1992 [DE] Germany .................. 42 24 698.9

[51] Int. Cl.$^6$ .............................................. H05F 1/00
[52] U.S. Cl. .................................... 361/214; 361/221
[58] Field of Search ................ 361/212, 214, 220, 221; 271/208; 474/90

[56] References Cited

U.S. PATENT DOCUMENTS

| | | | |
|---|---|---|---|
| 1,394,211 | 10/1921 | Morgan | 361/212 |
| 3,757,164 | 8/1973 | Binkowski | 261/221 |
| 4,307,432 | 12/1981 | Nishikawa | 361/221 |
| 4,363,070 | 12/1982 | Kisler | 361/212 |
| 4,402,035 | 8/1983 | Kisler | 361/221 |
| 4,454,559 | 6/1984 | Shenoy | 361/214 |
| 4,486,808 | 12/1984 | Cardone | 361/235 |
| 4,494,166 | 1/1985 | Billings et al. | 361/214 |
| 4,513,683 | 4/1985 | Kisler | 361/212 |
| 4,553,191 | 11/1985 | Franks, Jr. et al. | 361/212 |
| 4,771,360 | 9/1988 | Ayash | 361/221 |
| 4,825,334 | 4/1989 | Kisler | 361/212 |
| 4,851,874 | 7/1989 | Ogiyama | 355/253 |
| 5,010,441 | 4/1991 | Fox et al. | 361/221 |
| 5,041,941 | 8/1991 | Carter et al. | 361/225 |
| 5,059,990 | 10/1991 | Abreu et al. | 346/153 |
| 5,081,504 | 1/1992 | Morisawa et al. | 355/299 |

*Primary Examiner*—Jeffrey A. Gaffin
*Attorney, Agent, or Firm*—Lawrence P. Kessler

[57] ABSTRACT

Control of the neutralization of surface charges existing on objects such as paper, fabrics, plastic sheets or the like. In order that the surface of an object (1) can be neutralized independently of the output parameters, the electrostatic charge present on the object (1) is determined by means of a charge sensor (2) arranged upstream of the brush. The charge already neutralized via the brush (5) is also continuously measured. The two values are fed to a microprocessor (11) causing an actuator (7) to control the brush-to-object distance. The controlled movement of the brush (5) effects complete neutralization.

3 Claims, 1 Drawing Sheet

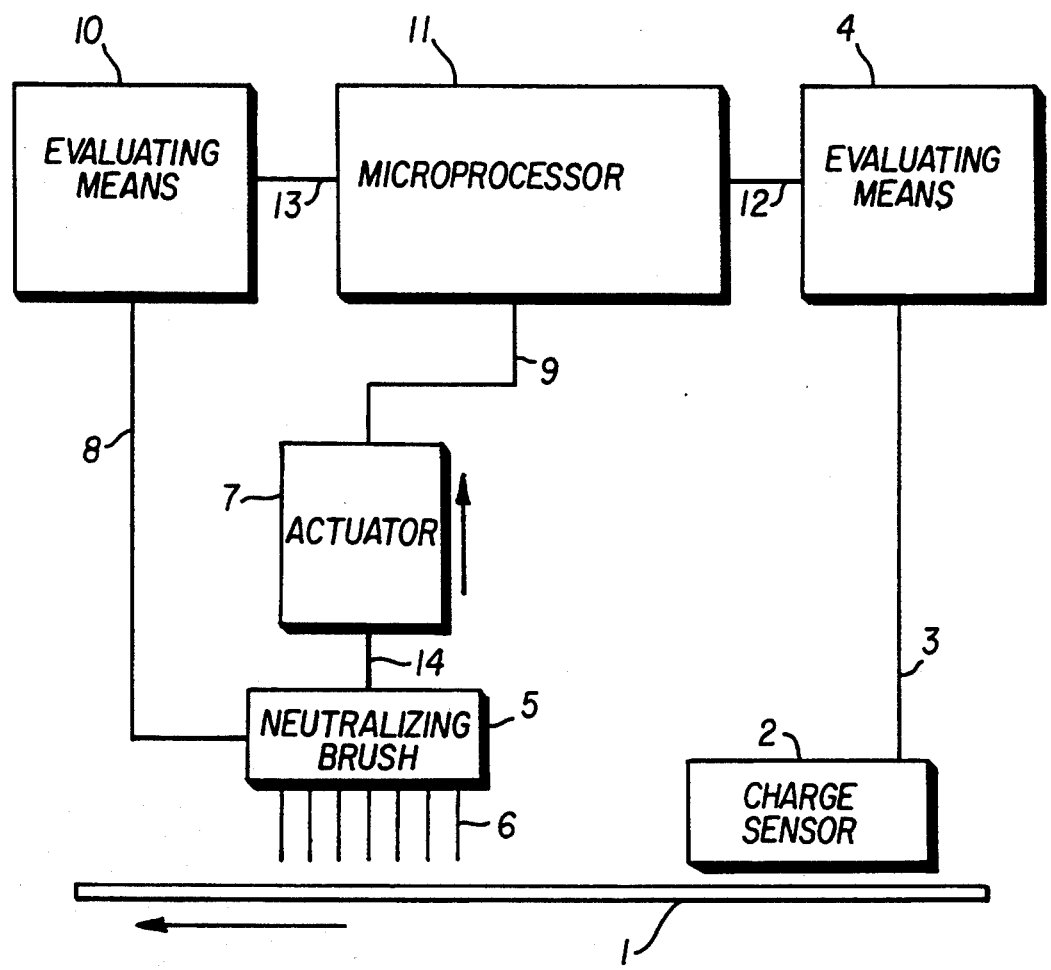

CONTROL OF THE NEUTRALIZATION OF SURFACE CHARGES ON OBJECTS

BACKGROUND OF THE INVENTION

The invention relates to control of the neutralization of surface charges existing on objects such as paper, fabrics, plastic sheets or the like.

It is well known to remove electrostatic charges from paper, fabrics, plastic sheets or the like by means of a brush which consists of thin conductive fibers, e.g., high-grade steel or carbon fibers, and neutralizes the charges. There are two methods utilized when employing such conductive fiber brush. The so-called passive discharge is based on the phenomenon that the breakdown field strength is exceeded and the ionized air molecules effect compensation of the surface charges. As a result, electric discharge current flows from the surface via the brush to ground. The active discharge method is based on corona discharge, the charge carriers being produced by applying high voltage to the fiber brush. Costly high-voltage supply, however, and ozone formation due to corona discharge are disadvantages of this latter method.

Neutralization of surface charges is effected by means of stationarily mounted brushes which remove the charges by mechanical contact with the surface. In DE-OS 29 50 192 A1, neutralization of electrostatic surface charges is described, the mechanical stress of the surface being kept as small as possible. Direct contact between surface and neutralizing brush is avoided by mounting an additional, non-conductive spacer element keeping the brush at a small distance (a few micrometers) from the surface. This method is based on the so-called corona discharge phenomenon according to which during the approach of a thin conductive wire towards a highly charged body an appropriate electrical field is produced on the periphery of the wire in order to effect ionization of a gas whereby the charged body is discharged. The above space elements prevent the brush from being soiled which would entail a reduction of the discharge properties of the brush. It is, however, a disadvantage that brush and object must be kept at a constant distance relative to each other throughout the process, and complete neutralization of the charge is achieved only when a certain charge condition exists.

U.S. Pat. No. 4,363,070 discloses a method in which the surface charges are neutralized without any contact between brush and object. A neutralizing brush is positioned at a distance of about 50 μm from the surface of the object and connected to an AC voltage source. The voltage source applies AC voltages across the brush and the grounded guide roller which vary both in frequency and amplitude. A charge sensor detects the actual surface charge condition which is compared with the nominal condition, a controlled variable being deduced therefrom and controlling the potential and/or the frequency of the AC voltage source so as to achieve complete neutralization of the surface. It is a disadvantage of this method that a high-voltage AC power supply is required and that it cannot react to thickness variations and/or to changes in the material properties of the object. When thickness or material properties of the object are changed, the brush position must be adjusted manually.

BRIEF DESCRIPTION OF THE DRAWING

The invention is described in detail with reference to an embodiment shown in the accompanying drawing.

The drawing, consisting of a block diagram shows the schematic setup of an arrangement for performing surface charge neutralization control according to the present invention.

DETAILED DESCRIPTION OF THE INVENTION

The preferred embodiment for the surface charge neutralization control according to this invention relates to paper transport within a copier or printer. A charge sensor 2 is positioned above the surface 1 to be sensed, e.g., paper, both endless or in sheet form. In order to simplify the description, the moving paper, fabric or plastic sheet is referred to as the "object." Downstream of the charge sensor 2 in the direction of object movement, neutralizing brush 5 is arranged which consists of thin conductive fibers 6. By means of an electro-mechanical actuator 7, as well known in the art, for example a worm drive, hydraulic cylinder, etc., the spacing between the brush 5 and the surface of the object 1 can be varied. For this purpose, the charge sensor 2 is connected to a first electronic evaluating means 4 via a line 3, and the brush 5 is connected to a second evaluating means 10 via a line 8. The two evaluating means 4 and 10 are connected to a microprocessor 11 via signaling lines 12 and 13, respectively. The microprocessor 11 is connected to an electro-mechanical actuator 7 via a line 9. Actuator 7 engages brush 5 by means of a mechanical connection 14. The first and second evaluating means 4 and 10 are devices to determine the charge amounts which include the appropriate circuitry well known in the art, see for example the specification OPA128 of BURR-BROWN, a corporation of Tucson Ariz.

The arrangement for the surface charge neutralization control according to this invention operates as follows:

Object 1 is moved in the direction of the arrow by means of a known transport device (not shown). In doing so, the surface charge $Q_p$ present on the surface of the object 1 is measured by the charge sensor 2. The measuring data are fed to a first evaluating means 4, processed, and then passed on via line 12 to the microprocessor 11 for further processing.

Via the neutralizing brush 5 located downstream, in the direction of object movement, of the charge sensor 2, the surface charges are removed through line 8 (and the second evaluating means 10) to zero ground potential. The second evaluating means 10 determines the magnitude of the discharge current. The two measuring signals produced by first and second evaluating means 4 and 10 are fed to the microprocessor 11 via the data lines 12 and 13, respectively. From the data received, the microprocessor 11 computes the charge $Q_e$ already neutralized and the residual charge $Q_{rest}$ i.e. $Q_p$-$Q_e$ still present on the surface. The quotient $W=Q_{rest}/Q_e$ is indicative of the efficiency of the neutralizing brush. The value $Q_{rest}$ must be minimal in order to effect complete neutralization of object 1.

For this purpose, the microprocessor 11 produces a control signal which, via line 9, is fed to an electromechanical actuator 7 connected to the brush by a means 14. According to quotients W determined and to the residual charge $Q_{rest}$, a control signal is produced setting the distance from the brush to the surface of object 1.

The residual charge $Q_{rest}$ and the charge $Q_e$ already neutralized are continuously determined as object 1 is advanced. The described method operates advantageously even if high atmospheric humidity prevails, since neutralization is then reached already at a relatively large distance between brush and object surface. Mechanical stress or physical damage of the surface of the object is thus minimized. Independent of the external and internal conditions, the method according to the invention always guarantees optimal neutralization of the static charge existing on the surface of an object.

The invention has been described in detail with particular reference to preferred embodiments thereof, but it will be understood that variations and modifications can be effected within the spirit and scope of the invention as set forth in the claims.

What is claimed is:

1. Apparatus for the neutralization of surface charges existing on objects (1), said charge neutralization apparatus comprising:
    a brush (5) including thin electrically conductive fibers for neutralizing the charges on a moving object;
    a charge sensor (2) arranged upstream, in the direction of object movement, of said brush (5);
    first electronic evaluating means (4), connected to said charge sensor (2), for determining the electrostatic charge ($Q_p$) present on the surface of the moving object (1);
    second electronic evaluating means (10), connected to said brush (5), for determining the already neutralized charge ($Q_e$);
    a microprocessor (11) connected to said first and second evaluating means (4 and 10), including means for comparing the electrostatic charge ($Q_p$) present on the surface of the moving object (1) and the already neutralized charge ($Q_e$) to determine the residual charge ($Q_{rest}$) on the surface of the moving object, and for producing a control signal based on such residual charge; and
    an actuator (7) engaging said brush (5) by a mechanical connection (14), said actuator being responsive to said control signal received from said microprocessor (11) for controlling the brush-to-object distance.

2. Method of controlling the neutralization of surface charges existing on objects such as paper, fabrics, plastic sheets or the like comprising:
    determining the electrostatic charge ($Q_p$) present on the surface of an object (1);
    determining the already neutralized charge ($Q_e$), by measuring the charge current flowing across a charge neutralizing brush (5);
    comparing the two determined values ($Q_p$ and $Q_e$) to determine the residual charge ($Q_{rest}$);
    producing a control signal based upon ($Q_{rest}$) for controlling the spacing between the neutralization brush (5) and the surface of the object (1); and
    completing the neutralization of the charges within the time of the passage of the object (1).

3. The method of controlling the neutralization of surface charges according to claim 2 wherein the producing of the control signal is effected continuously.

* * * * *